United States Patent
DeLuca et al.

(10) Patent No.: US 7,238,681 B2
(45) Date of Patent: Jul. 3, 2007

(54) 2-METHYLENE-18,19-DINOR-1α-HYDROXY-HOMOPREGNACALCIFEROL AND ITS USES

(75) Inventors: Hector F. DeLuca, Deerfield, WI (US); Rafal Barycki, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/283,222

(22) Filed: Nov. 18, 2005

(65) Prior Publication Data

US 2006/0122157 A1 Jun. 8, 2006

Related U.S. Application Data

(60) Provisional application No. 60/630,182, filed on Nov. 22, 2004.

(51) Int. Cl.
*A61K 31/59* (2006.01)
*C07D 401/00* (2006.01)
(52) U.S. Cl. .................................. 514/167; 552/653
(58) Field of Classification Search ............. 514/167; 552/653
See application file for complete search history.

(56) References Cited

U.S. PATENT DOCUMENTS

| 5,843,928 | A | | 12/1998 | DeLuca et al. | |
|---|---|---|---|---|---|
| 5,945,410 | A | * | 8/1999 | DeLuca et al. | 514/167 |
| 6,440,953 | B1 | * | 8/2002 | DeLuca et al. | 514/167 |
| 6,579,861 | B2 | | 6/2003 | DeLuca et al. | |
| 6,627,622 | B2 | * | 9/2003 | DeLuca et al. | 514/167 |
| 6,774,251 | B2 | * | 8/2004 | DeLuca et al. | 552/653 |
| 6,846,811 | B2 | * | 1/2005 | DeLuca et al. | 514/167 |
| 6,887,860 | B2 | * | 5/2005 | DeLuca et al. | 514/167 |
| 7,094,916 | B2 | * | 8/2006 | DeLuca et al. | 552/653 |

* cited by examiner

*Primary Examiner*—Sabiha N. Qazi
(74) *Attorney, Agent, or Firm*—Andrus, Sceales, Starke & Sawall, LLP

(57) ABSTRACT

This invention discloses 2-methylene-18,19-dinor-vitamin D analogs, and specifically 2-methylene-18,19-dinor-1α-hydroxy-homopregnacalciferol and pharmaceutical uses therefor. This compound exhibits pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also has little, if any, calcemic activity and therefore may be used to treat autoimmune disorders or inflammatory diseases in humans as well as renal osteodystrophy. This compound may also be used for the treatment or prevention of obesity.

79 Claims, 5 Drawing Sheets

2-METHYLENE-18,19-DINOR-1α-HYDROXY-HOMOPREGNACALCIFEROL AND ITS USES

CROSS REFERENCE TO RELATED APPLICATION

This application claims priority to U.S. Provisional Application No. 60/630,182, filed Nov. 22, 2004.

BACKGROUND OF THE INVENTION

This invention relates to vitamin D compounds, and more particularly to 2-methylene-18,19-dinor-1α-hydroxy-homopregnacalciferol and its pharmaceutical uses.

The natural hormone, 1α,25-dihydroxyvitamin $D_3$ and its analog in the ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptor and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The present invention is directed toward 2-methylene-18,19-dinor-vitamin D analogs, and more specifically toward 2-methylene-18,19-dinor-1α-hydroxy-homopregnacalciferol, their biological activity, and various pharmaceutical uses for these compounds.

Structurally these 2-methylene-18,19-dinor-vitamin D analogs are characterized by the general formula I shown below:

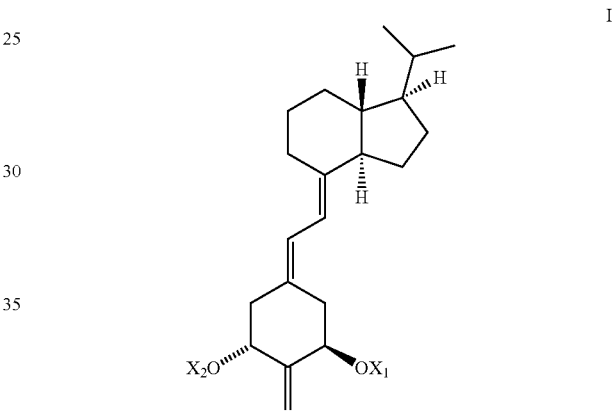

where $X_1$ and $X_2$, which may be the same or different, are each selected from hydrogen or a hydroxy-protecting group. The preferred analog is 2-methylene-18,19-dinor-1α-hydroxy-homopregnacalciferol which has the following formula Ia:

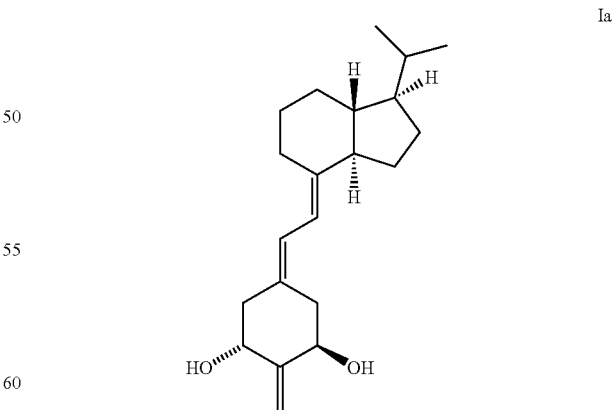

The above compounds I, and particularly Ia, exhibit a desired, and highly advantageous, pattern of biological activity. These compounds are characterized by relatively high binding to vitamin D receptors, but very low intestinal calcium transport activity, as compared to that of 1α,25-dihydroxyvitamin $D_3$, and have very low ability to mobilize calcium from bone, as compared to 1α,25-dihydroxyvitamin $D_3$. Hence, these compounds can be characterized as having little, if any, calcemic activity. It is undesirable to raise serum calcium to supraphysiologic levels when suppressing the preproparathyroid hormone gene (Darwish & DeLuca, Arch. Biochem. Biophys. 365, 123–130, 1999) and parathyroid gland proliferation. These analogs having little or no calcemic activity while very active on differentiation are expected to be useful as a therapy for suppression of secondary hyperparathyroidism of renal osteodystrophy.

The compounds I, and particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity. Thus, these compounds also provide therapeutic agents for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of 18,19-dinor-2MP and 1,25(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of 18,19-dinor-2MP and 1,25(OH)$_2$D$_3$;

FIG. 3 is a graph illustrating the in vitro transcription activity of 1,25(OH)$_2$D$_3$ as compared to 18,19-dinor-2MP;

FIG. 4 is a bar graph illustrating the bone calcium mobilization activity of 1,25(OH)$_2$D$_3$ as well as the compound 2-methylene-19-nor-1α-hydroxy-homopregnacalciferol (hereinafter referred to as "2-MP"), as compared to 18,19-dinor-2MP; and FIG. 5 is a bar graph illustrating the intestinal calcium transport activity of 1,25(OH)$_2$D$_3$ as well as 2-MP, as compared to 18,19-dinor-2MP.

Figure 1:
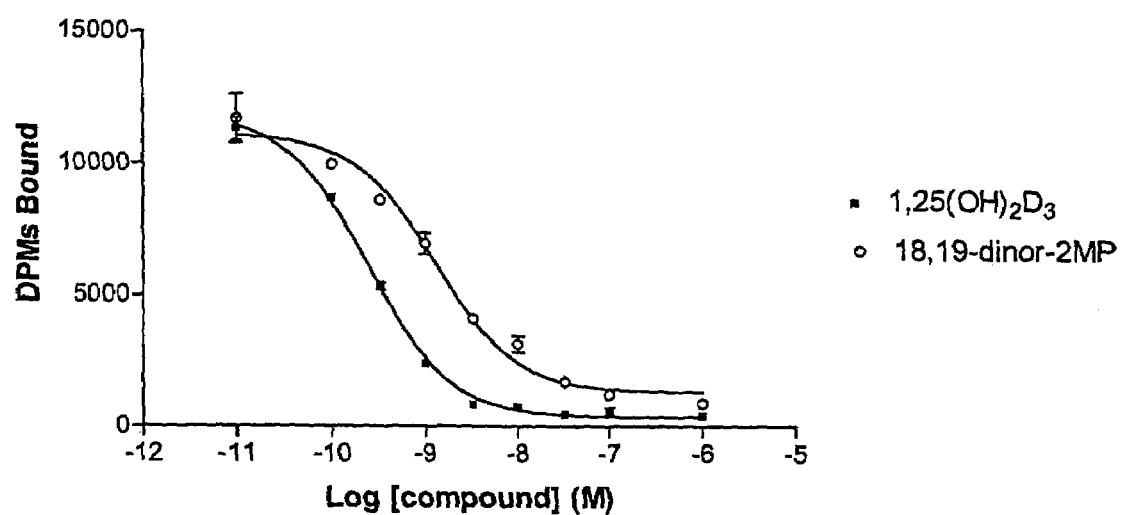
FIGS. 1–5 illustrate various biological activities of 2-methylene-18,19-dinor-1α-hydroxy-homopregnacalciferol, hereinafter referred to as "18,19-dinor-2MP," as compared to the native hormone 1α,25-dihydroxyvitamin $D_3$, hereinafter "1,25(OH)$_2$D$_3$."

DETAILED DESCRIPTION OF THE INVENTION 2-methylene-18,19-dinor-1α-hydroxy-homopregnacalciferol (referred to herein as 18,19-dinor-2MP) was synthesized and tested. Structurally, this 2-methylene-18,19-dinor vitamin D analog is characterized by the general formula Ia previously illustrated herein, and its pro-drug (in protected hydroxy form) is characterized by general formula I previously illustrated herein.

The preparation of 2-methylene-18,19-dinor-1α-hydroxy-homopregnacalciferol having the structure Ia and its pro-drug can be accomplished by a common general method, i.e. the condensation of a bicyclic Windaus-Grundmann type ketone II with the allylic phosphine oxide III to the corresponding 2-methylene-18,19-dinor-vitamin D analog IV followed by deprotection at C-1 and C-3 in the latter compound:

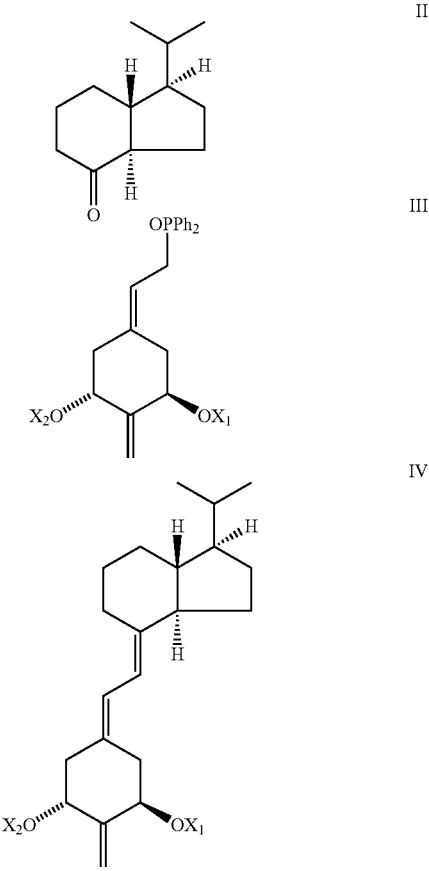

In the structures III and IV, groups $X_1$ and $X_2$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown on Scheme I herein (see the preparation of compound 18,19-dinor-2MP).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is similar to the process described in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following description as well as to Scheme 1 herein for a detailed illustration of the preparation of compound 18,19-dinor-2MP.

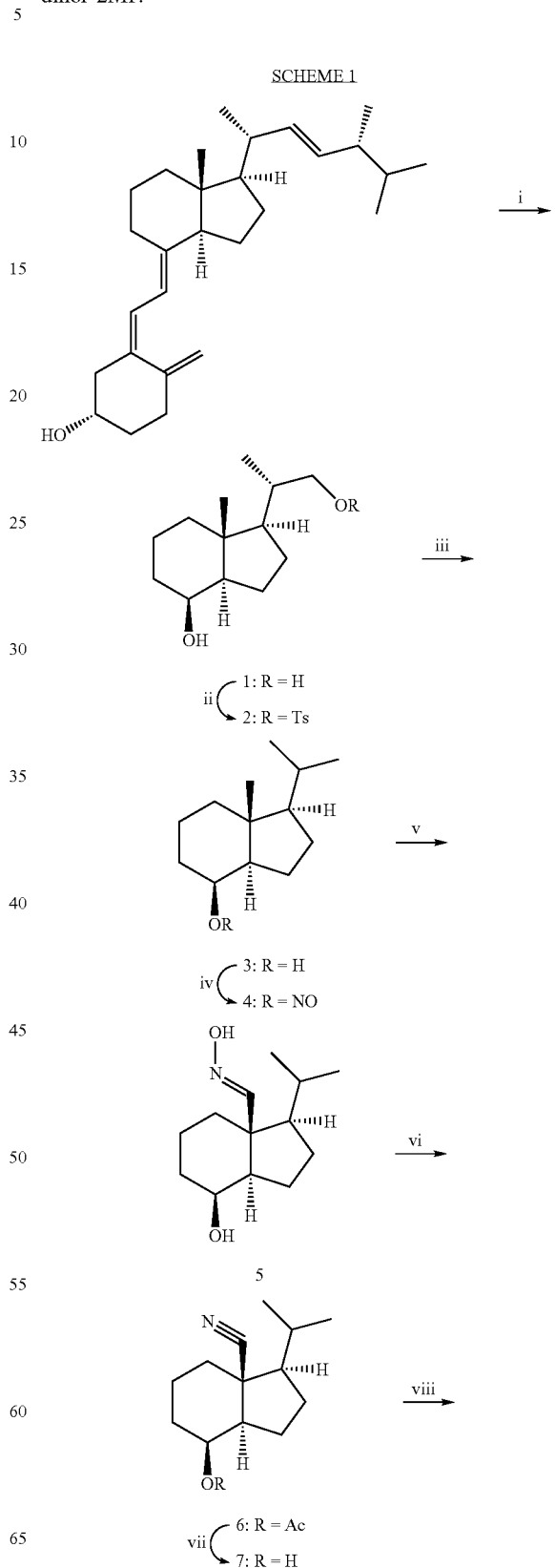

SCHEME 1

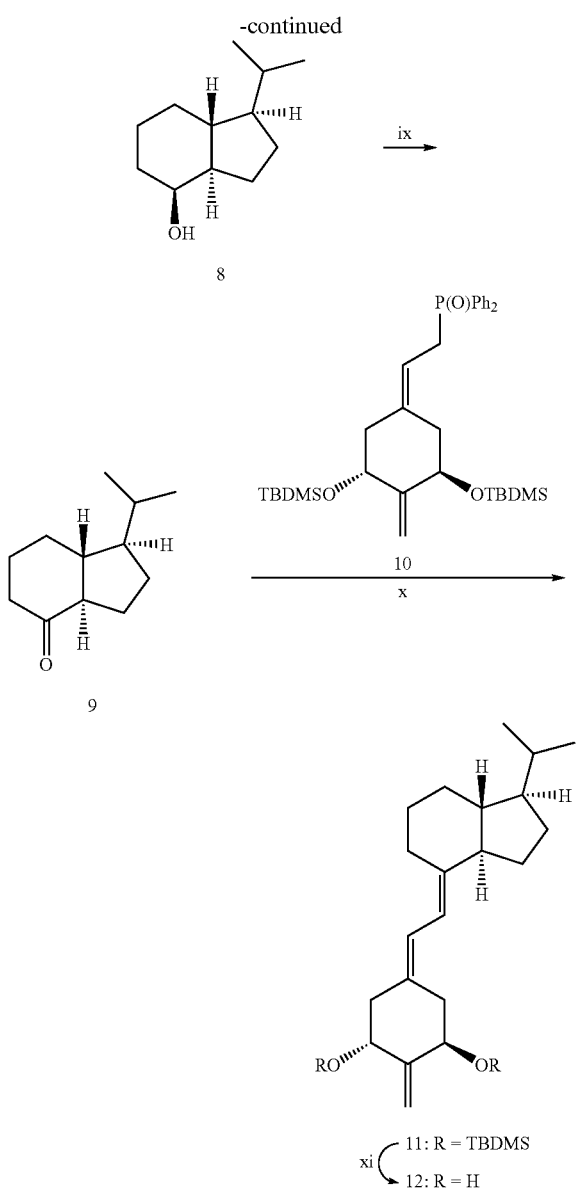

(i) O₃, MeOH, py; NaBH₄, 76%.
(ii) TsCl, Et₃N, DMAP, CH₂Cl₂, 97%.
(iii) LiAlH₄, Et₂O, 85%.
(iv) t-BuONO, CHCl₃.
(v) hv, C₆H₆; i-PrOH, 67% (from 3).
(vi) AcO, 98%.
(vii) MeONa/MeOH, 97%.
(viii) K, HMPA, t-BuOH, Et₂O, 69%.
(ix) PDC, PPTS, CH₂Cl₂, 81%.
(x) 10, PhLi, THF, 64%.
(xi) CSA, n-BuOH, 93%.

Des-A,B-23,24-dinorcholane-8β,22-diol (1). A solution of vitamin D₂ (5 g, 12.7 mmol) in methanol (400 mL) and pyridine (5 mL) was cooled to −78° C. while purging with argon. The argon stream was stopped and stream of ozone was passed until blue color appeared. The solution was purged with oxygen until blue color disappeared and treated with NaBH₄ (1.2 g, 32 mmol). After 20 min. the second portion of NaBH₄ (1.2 g, 32 mmol) was added and reaction was allowed to warm to room temperature. The third portion of NaBH₄ (1.2 g, 32 mmol) was added and reaction mixture was stirred at room temperature overnight. The reaction was quenched with 70 mL of water and concentrated under vacuum. The residue was extracted with methylene chloride (3×100 mL). The organic phase was washed with 1M aqueous solution of HCl (2×100 mL), saturated aqueous solution of NaHCO₃ (100 mL), dried over anhydrous MgSO₄ and concentrated under vacuum. The residue was purified by flash chromatography (25% ethyl acetate/hexane) to yield 2.05 g (9.69 mmol, 76% yield) of diol 1 as white crystals. $[\alpha]_D$+56.0 (c 0.95, CHCl₃); mp 110–111° C.; ¹H NMR (400 MHz, CDCl₃) δ 0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); ¹³C NMR (100 MHz, CDCl₃) δ 13.6, 16.6, 17.4, 22.6, 26.6, 33.5, 38.2, 40.2, 41.3, 52.3, 52.9, 67.8, 69.2; MS (EI) m/z 212 (2, M⁺), 194 (17), 179 (18), 163 (10), 135 (19), 125 (34), 111 (100); exact mass calculated for C₁₃H₂₂O ([M−H₂O]⁺) 194.1671, found 194.1665.

Des-A,B-23,24-dinor-22-(tosyloxy)cholane-8β-ol (2). To a stirred solution of 1 (450 mg, 2.12 mmol), triethylamine (975 μL, 708 mg, 7.00 mmol) and DMAP (20 mg, 0.16 mmol) in anhydrous methylene dichloride (20 mL) tosyl chloride was added at 0° C. The reaction mixture was kept at 4° C. overnight. Then methylene dichloride (30 mL) was added and the reaction mixture was washed with saturated aqueous solution of NaHCO₃ (2×30 mL), dried over anhydrous Na₂SO₄ and concentrated under reduced pressure. The residue was purified by column chromatography (25–30% ethyl acetate/hexane) to give 754 mg (2.06 mmol, 97% yield) of 2. $[\alpha]_D$+21.0 (c 1.10, CHCl₃); ¹H NMR (500 MHz, CDCl₃) δ 0.89 (3H, s), 0.96 (3H, d, J=6.7 Hz), 2.45 (3H, s), 3.81 (1H, dd, J=9.2 Hz, J=6.2 Hz), 3.95 (2H, dd, J=9.2 Hz, J=3.0 Hz) 4.07 (1H, br d), 7.34 (2H, d, J=8.2 Hz), 7.78 (2H, d, J=8.2 Hz); ¹³C NMR (125 MHz, CDCl₃) δ 13.4, 16.8, 17.3, 21.6, 22.4, 26.4, 33.5, 35.7, 40.0, 41.8, 52.2, 69.0, 75.6, 127.9, 129.8, 133.1, 144.6; MS (EI) m/z 366 (7, M⁺), 348 (5), 194 (16), 179 (19), 161 (11), 155 (19), 150 (16), 135 (15), 125 (37), 111 (100); exact mass calculated for C₂₀H₃₀O₄S 366.1865, found 366.1876.

Des-A,B-23,24-dinorcholane-8β-ol (3). To a stirred slurry of LiAlH₄ (290 mg, 7.65 mmol) in diethyl ether (30 mL) a solution of 2 (700 mg, 1.91 mmol) in diethyl ether (20 mL) was added dropwise via cannula. The reaction mixture was stirred for 1 h under argon. Then several drops of ethyl acetate, 5% aqueous solution of HCl (25 mL, at 0° C.) and water (30 mL) were added and the mixture was extracted with diethyl ether (3×40 mL). Organic phase was dried over anhydrous Na₂SO₄, concentrated under reduced pressure and the residue was purified by column chromatography (5–10% ethyl acetate/hexane) to give 320 mg (1.60 mmol, 85% yield) of 3. $[\alpha]_D$+23.5 (c 0.90, CHCl₃); ¹H NMR (400 MHz, CDCl₃) δ 0.84 (3H, d, J=6.6 Hz), 0.91–0.93 (6H, m), 4.07 (1H, br d, J=2.2 Hz); ³C NMR (100 MHz, CDCl₃) δ 13.6, 17.4, 22.4, 22.5, 23.0, 27.4, 30.5, 33.5, 40.3, 41.8, 52.6, 58.7, 69.4; MS (EI) m/z 196 (15, M⁺), 181 (16), 135 (13), 125 (16), 111 (100); exact mass calculated for C₁₃H₂₄O 196.1827, found 196.1828.

Des-A,B-23,24-dinorcholane-8β-yl nitrite (4). To a stirred solution of 3 (285 mg, 1.53 mmol) in chloroform (8 mL) tert-butyl nitrite (2.2 mL) was added dropwise in darkness. After 1 h benzene was added and solvents were removed under reduced pressure.

(18E)-18-(Hydroxyimino)-des-A,B-23,24-dinorcholane-8β-ol (5). Crude nitrite was dissolved in anhydrous benzene (150 mL) and irradiated in an apparatus consisting of a Pyrex vessel with a watercooled immersion well and Hanovia high-pressure mercury arc lamp equipped with Pyrex filter. A slow stream of argon was passed through solution and temperature was maintained at about 10° C. A reaction progress was monitored by TLC. After 45 min. reaction was completed. Benzene was removed under reduced pressure and the residue was dissolved in 2-propanol (5 mL) and kept overnight to accomplish isomerisation of a nitroso compound to an oxime. The solvent was evaporated and the residue was purified on Waters silica gel Sep-Pack cartridge (15–25% ethyl acetate/hexane) to give 230 mg (1.02 mmol, 67% yield starting from 3) of 5. $[\alpha]_D$+45.7 (c 0.90, CHCl$_3$); mp. 144° C.; $^1$H NMR (400 CDCl$_3$) δ 0.88 (3H, d, J=6.5 Hz), 1.02 (3H, d, J=6.5 Hz), 2.20 (1H, d, J=13.2 Hz), 4.04 (1H, s), 6.78 (1H, s), 7.34 (1H, s), 10.94 (1H, s); $^{13}$C NMR (100 MHz, CDCl$_3$) δ 17.4, 21.9, 22.3, 23.1, 27.7, 30.9, 34.2, 36.5, 49.5, 52.5, 58.9, 67.5, 151.9; MS (EI) m/z 225 (20, M$^+$), 208 (92), 190 (70), 183 (78), 175 (40), 164 (43), 136 (66), 121 (51), 87 (100); exact mass (ESI) calculated for C$_{13}$H$_{23}$NO$_2$Na ([M+Na]$^+$) 248.1626, found 248.1620.

8β-(Acetoxy)-des-A,B-23,24-dinorcholane-18-nitrile (6). A solution of 5 (220 mg, 0.98 mmol) in acetic anhydride (15 mL) was refluxed for 1.5 h. The reaction mixture was cooled, poured carefully into ice and extracted with benzene (3×60 mL). Combined organic phases were washed with saturated aqueous solution of NaHCO$_3$ (2×50 mL), water (30 mL), dried over anhydrous Na$_2$SO$_4$ and evaporated. The residue was purified on Waters silica gel Sep-Pack cartridge (8–10% ethyl acetate/hexane) to give 239 mg (0.96 mmol, 98% yield) of 6. $[\alpha]_D$−5.2 (c 0.95, CHCl$_3$); mp. 40° C.; $^1$H NMR (400 MHz, CDCl$_3$) δ 0.94 (3H, d, J=6.6 Hz), 1.05 (3H, d, J=6.6 Hz), 2.14 (3H, s), 2.49 (1H, br d, J=13.8 Hz), 5.20 (1H, s); $^{13}$C NMR (100 MHz, CDCl$_3$) δ 18.7, 20.9, 22.3, 23.4, 27.4, 29.8, 32.1, 36.2, 45.7, 51.9, 56.2, 68.6, 121.1, 170.9; MS (EI) m/z 249 (2, M$^+$), 224 (9), 207 (66), 189 (43), 183 (100); exact mass calculated for C$_{15}$H$_{23}$NO$_2$ 249.1729, found 249.1733.

Des-A,B-23,24-dinorcholane-18-nitrile-8β-ol (7). 6 (225 mg, 0.90 mmol) was dissolved in methanol (10 mL) and treated with 10% solution of MeONa in methanol (10 mL) for 2 h. After that solvent was removed under reduced pressure, the residue was treated water (20 mL) and saturated aqueous solution of NH$_4$Cl (15 mL) and extracted with methylene dichloride (3×50 mL). Organic phase was dried over anhydrous Na$_2$SO$_4$ and evaporated. The residue was purified on Waters silica gel Sep-Pack cartridge (20–30% ethyl acetate/hexane) to give 180 mg (0.87 mmol, 97% yield) of 7. $[\alpha]_D$+20.6 (c 1.15, CHCl$_3$); $^1$H NMR (500 MHz, CDCl$_3$) δ 0.94 (3H, d, J=6.6 Hz), 1.04 (3H, d, J=6.6 Hz), 2.46 (1H, br d, J=13.0 Hz), 4.11 (1H, m); $^{13}$C NMR (125 MHz, CDCl$_3$) δ 18.0, 22.2, 22.2, 23.0, 27.5, 32.0, 32.7, 36.3, 44.9, 53.4, 56.2, 67.4, 122.3; MS (EI) m/z 207 (14, M$^+$), 180 (16), 174 (26), 162 (39), 147 (20), 136 (39), 121 (100); exact mass calculated for C$_{13}$H$_{21}$NO 207.1623, found 207.1618.

Des-A,B-18,23,24-trinorcholane-8β-ol (8). To a stirred mixture of potassium (270 mg, 6.75 mmol) in HMPA (950 μL, 979 mg, 5.46 mmol) and diethyl ether (2 mL) a solution of 7 (185 mg, 0.89 mmol) in tert-butyl alcohol (220 μL) and diethyl ether (850 μL) was added dropwise at 0° C. under argon. The mixture was allowed to warm up to room temperature and stirred overnight. Remaining potassium was removed, a few drops of 2-propanol and benzene (40 mL) were added. Organic phase was washed with water (10 mL), dried over anhydrous Na$_2$SO$_4$ and concentrated under reduced pressure. The residue was purified on Waters silica gel Sep-Pack cartridge (5–10% ethyl acetate/hexane) to give 112 mg (0.62 mmol, 69% yield) of 8. $[\alpha]_D$+54.9 (c 0.85, CHCl$_3$); $^1$H NMR (500 MHz, CDCl$_3$) δ 0.82 (3H, d, J=6.8 Hz), 0.90 (3H, d, J=6.8 Hz), 1.83 (1H, br dd, J=13.4 Hz, J=2.3 Hz), 1.92 (1H, br dd, J=12.5 Hz, J=2.3 Hz), 4.07 (1H, s); $^{13}$C NMR (125 MHz, CDCl$_3$) δ 18.1, 20.1, 21.8, 24.0, 24.6, 29.4, 31.1, 33.2, 40.1, 50.1, 50.3, 67.9; MS (EI) m/z 163 (4), 149 (3), 139 (12), 121 (100); exact mass calculated for C$_9$H$_{15}$O ([M−C$_3$H$_7$]$^+$) 139.1123, found 139.1124.

Des-A,B-18,23,24-trinorcholane-8β-one (9). To a stirred solution of 8 (15 mg, 82 μmol) and PPTS (2 crystals) in methylene dichloride (4 mL) PDC (110 mg, 290 μmol) was added at 0° C. After 5 min. cooling bath was removed and the reaction mixture was stirred for 6 h. Then solvent was removed under reduced pressure and the residue was purified on Waters silica gel Sep-Pack cartridge (2–5% ethyl acetate/hexane) to give 12 mg (67 μmol, 81% yield) of 9. $^1$H NMR (400 MHz, CDCl$_3$) δ 0.82 (3H, d, J=6.8 Hz), 0.92 (3H, d, J=6.8 Hz); $^{13}$C NMR (100 MHz, CDCl$_3$) δ 18.0, 21.4, 21.6, 24.1, 27.8, 29.3, 30.3, 41.5, 51.3, 51.6, 58.3, 212.0; MS (EI) m/z 180 (40, M$^+$), 137 (100); exact mass calculated for C$_{12}$H$_{20}$O 180.1514, found 180.1520.

2-Methylene-18,19-dinor-1α-hydroxy-homopregnacalciferol (12). To a stirred solution of phosphine oxide 10 (45 mg, 77 μmol) in anhydrous THF (600 μl) a 1.5 M solution of phenyl lithium in THF (75 μl, 105 μmol) was added at −20° C. under argon. The mixture was stirred for 20 min. and then cooled to −78° C. A precooled solution of 9 (6 mg, 33 μmol) in anhydrous THF (200 μl) was added via cannula and the reaction mixture was stirred for 3 h at −78° C. After that the reaction mixture was stirred at 4° C. overnight. Then ethyl acetate was added and organic phase was washed with brine, dried over anhydrous Na$_2$SO$_4$ and concentrated under reduced pressure. The residue was purified on Waters silica gel Sep-Pack cartridge (hexane to 3% ethyl acetate/hexane) and then on HPLC (0.03% 2-propanol/hexane, 4 mL/min., Zorbax-silica 10×250 mm) to give 11.4 mg (21 mmol, 64% yield) of 11 at R$_t$=7.08 min. UV (hexane) λ$_{max}$=242, 250, 261 nm; $^1$H NMR (400 MHz, CDCl$_3$) δ 0.03 (3H, s), 0.04 (3H, s), 0.07 (3H, s), 0.08 (3H, s), 0.80 (3H, d, J=6.8 Hz), 0.86 (9H, s), 0.89 (9H, s), 2.18 (1H, dd, J=12.4 Hz, J=7.7 Hz), 2.86 (1H, br d, J=13.8 Hz), 4.42 (1H, m), 4.93 (1H, s), 4.96 (1H, s), 5.93 (1H, d, J=11.2 Hz), 6.20 (1H, d, J=11.2 Hz); $^{13}$C NMR (100 MHz, CDCl$_3$) δ−5.1, −4.9, −4.8, 18.2, 18.2, 18.3, 21.6, 24.6, 25.8, 25.8, 27.8, 28.9, 29.8, 31.9, 38.7, 47.5, 50.7, 50.8, 52.7, 71.9, 72.3, 106.3, 113.7, 122.4, 132.9, 143.7, 153.0; MS (EI) m/z 544 (3, M$^+$), 448 (9), 412 (36), 366 (14), 313 (11), 290 (100); exact mass calculated for C$_{33}$H$_{60}$O$_2$Si$_2$ 544.4132, found 544.4131.

To a stirred solution of 11 (11 mg, 20 μmol) in anhydrous n-butanol (1 mL) (1S)-(+)-10-camphorsulfonic acid (7 mg, 30 μmol) was added at 0° C. Then cooling bath was removed and the reaction mixture was stirred for 4 days. After that saturated aqueous solution of NaHCO$_3$ (1 mL) and water (3 mL) were added and the mixture was extracted with ethyl acetate (3×7 mL). Organic phase was dried over anhydrous Na$_2$SO$_4$, concentrated under reduced pressure and the residue was purified on Waters silica gel Sep-Pack cartridge (20–30% ethyl acetate/hexane). Crude vitamin was repurified on HPLC (10% 2-propanol/hexane, 4 mL/min., Zorbax-silica 10×250 mm) to give 6 mg (19 μmol, 93% yield) of 12 at R$_t$=7.78 min. UV (EtOH) λ$_{max}$=242, 250, 260 nm; $^1$H NMR (400 MHz, CDCl$_3$) δ 0.80 (3H, d, J=6.8 Hz), 0.88 (3H, d, J=6.8 Hz), 2.58 (1H, dd, J=13.2 Hz, J=3.8 Hz), 4.48 (1H, br s), 5.09 (1H, s), 5.10 (1H, s), 5.97 (1H, d, J=11.3 Hz), 6.35 (1H, d, J=11.3 Hz); $^{13}$C NMR (100 MHz, CDCl$_3$) δ 18.3, 21.7, 24.5, 25.8, 27.8, 29.1, 29.8, 31.7, 38.0, 45.9, 50.7, 50.9, 52.7, 70.9, 71.7, 107.7, 112.9, 124.3, 130.7, 146.0, 152.0; MS (EI) m/z 316 (14, M+), 298 (10), 280 (15), 237 (19), 84 (71), 66 (100); exact mass calculated for $C_{21}H_{32}O_2$ 316.2402, found 316.2387.

Biological Activity of 2-Methylene-18,19-Dinor-1α-Hydroxy-Homopregnacalciferol

The introduction of a methylene group to the 2-position, the substitution of a hydrogen for the methyl normally found at the 18 position, and the elimination of carbons 23, 24, 25, 26 and 27 in the side chain of 1α-hydroxy-19-nor-vitamin $D_3$ had little or no effect on binding to the full length recombinant rat vitamin D receptor, as compared to 1α,25-dihydroxyvitamin $D_3$. The compound 18,19-dinor-2MP bound one-fifth as well to the receptor as compared to the standard 1,25-$(OH)_2D_3$ (FIG. 1). It might be expected from these results that compound 18,19-dinor-2MP would have similar biological activity. Surprisingly, however, compound 18,19-dinor-2MP is a highly selective analog with unique biological activity.

Figure 5:
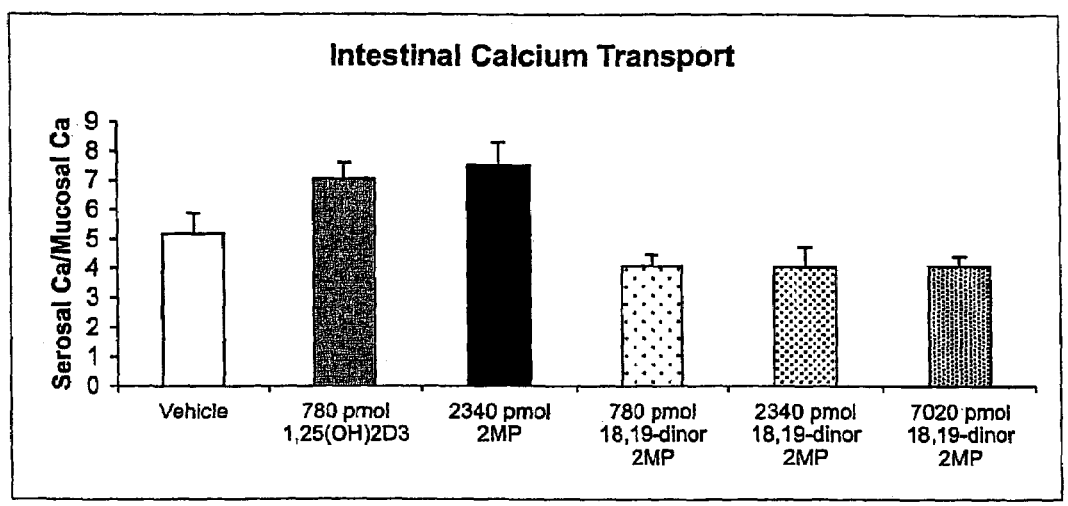

FIG. 5 shows that 18,19-dinor-2MP has no measurable activity as compared to that of 1,25-dihydroxyvitamin $D_3$ (1,25$(OH)_2D_3$), the natural hormone, in stimulating intestinal calcium transport.

Figure 4:
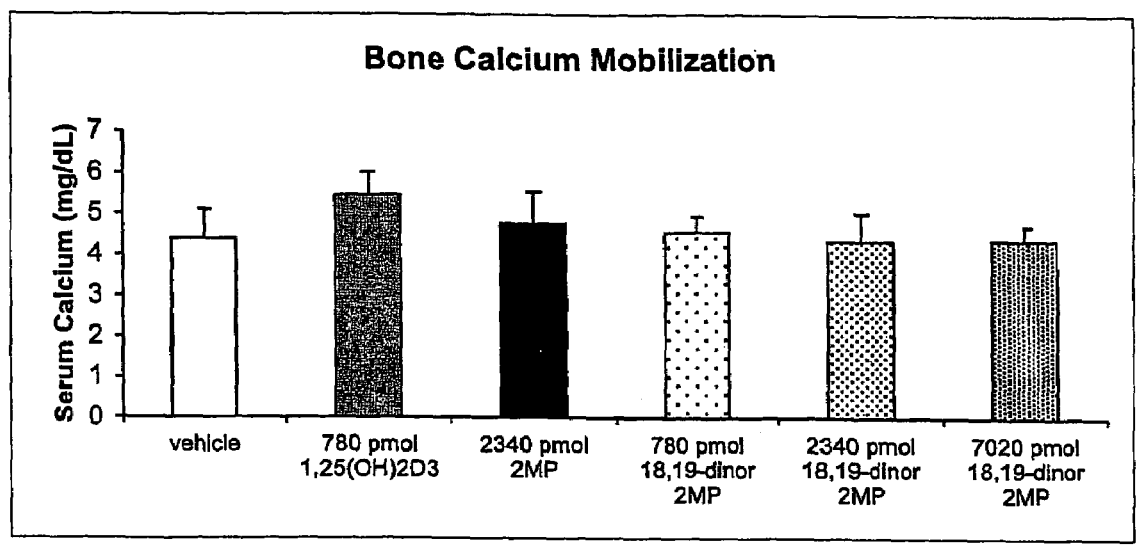

FIG. 4 demonstrates that 18,19-dinor-2MP has no measurable bone calcium mobilization activity, as compared to 1,25$(OH)_2D_3$.

FIGS. 4 and 5 thus illustrate that 18,19-dinor-2MP may be characterized as having little, if any, calcemic activity.

Figure 2:
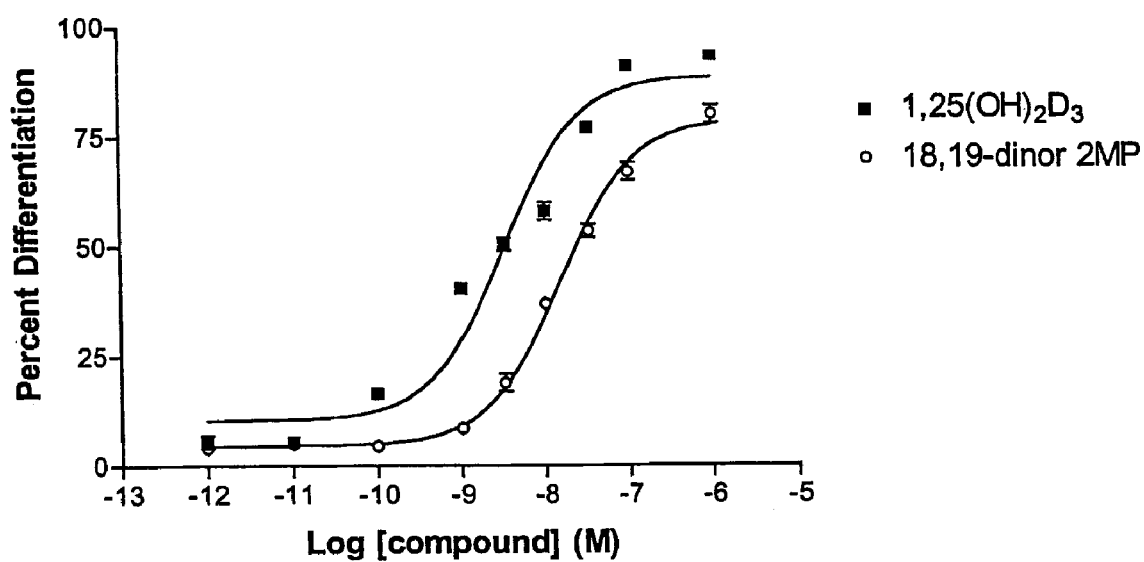

FIG. 2 illustrates that 18,19-dinor-2MP is almost as potent as 1,25$(OH)_2D_3$ on HL-60 cell differentiation, making it an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
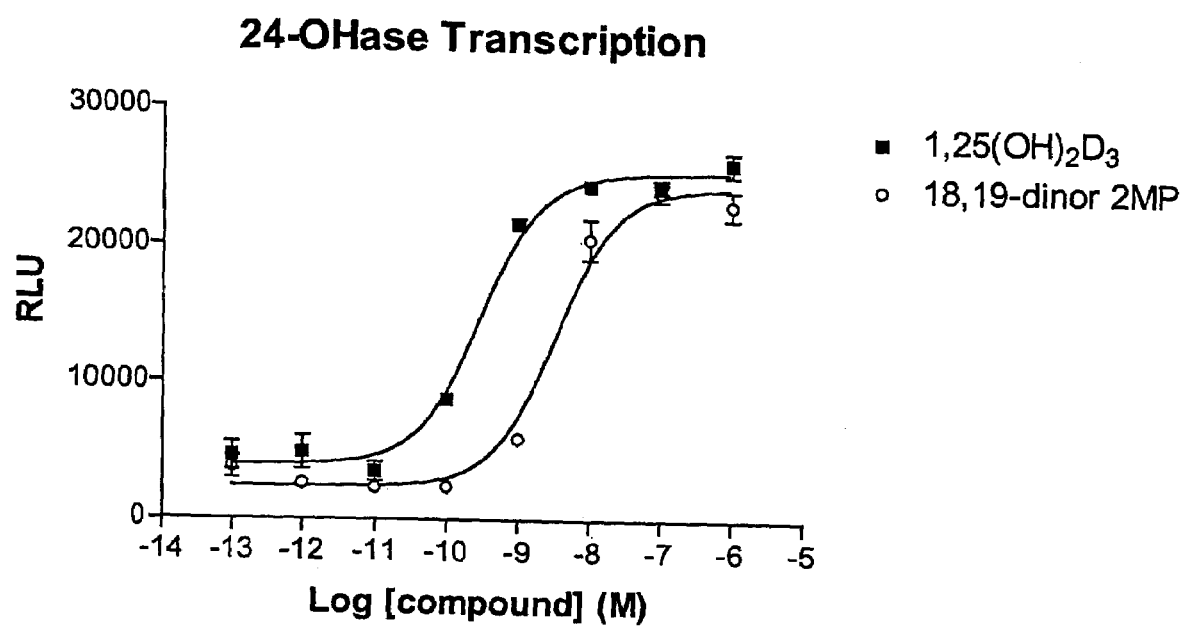

FIG. 3 illustrates that the compound 18,19-dinor-2MP has one-tenth the transcriptional activity of 1α,25-dihydroxyvitamin $D_3$ in bone cells. This result, together with the cell differentiation activity of FIG. 2, suggests that 18,19-dinor-2MP will be very effective in psoriasis because it has direct cellular activity in causing cell differentiation and in suppressing cell growth. These data also indicate that 18,19-dinor-2MP may have significant activity as an anti-cancer agent, especially against leukemia, colon cancer, breast cancer, skin cancer and prostate cancer.

The strong activity of 18,19-dinor-2MP on HL-60 differentiation and increasing gene transcription suggest it will be active in suppressing growth of parathyroid glands and in the suppression of the preproparathyroid gene.

Experimental Methods

Vitamin D Receptor Binding

Test Material

Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25$(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at 1.2×10⁵ cells/ml. Eighteen hours after plating, cells in duplicate were treated with drug. Four days later, the cells were harvested and a nitro blue tetrazolium reduction assay was performed (Collins et al., 1979; J. Exp. Med. 149:969–974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.
RLU=relative luciferase units.

Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

VDR binding, HL60 cell differentiation, and transcription activity. 18,19-dinor-2MP ($K_i=2.2\times10^{-10}$M) is slightly less active compared the natural hormone 1α,25-dihydroxyvitamin $D_3$ ($K_i=4.1\times10^{-11}$M) in its ability to compete with [$^3$H]-1,25(OH)$_2$D$_3$ for binding to the full-length recombinant rat vitamin D receptor (FIG. 1). Compound 18,19-dinor-2MP (EC$_{50}$=1.5×10$^{-8}$M) is a little less active in promoting HL60 differentiation as compared to 1α,25-dihydroxyvitamin $D_3$ (EC$_{50}$=3.2×10$^{-9}$M) (See FIG. 2). Also, compound 18,19-dinor-2MP (EC$_{50}$=1.5×10$^{-8}$M) has transcriptional activity in bone cells that is a little less than 1α,25-dihydroxyvitamin $D_3$ (EC$_{50}$=3.2×10$^{-9}$M) (See FIG. 3). These results suggest that 18,19-dinor-2MP will be very effective in psoriasis because it has direct cellular activity in causing cell differentiation and in suppressing cell growth. These data also indicate that 18,19-dinor-2MP will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of 18,19-dinor-2MP and 1,25(OH)$_2$D$_3$ in intestine and bone were tested. As expected, the native hormone (1,25 (OH)$_2$D$_3$) increased serum calcium levels at all dosages (FIG. 4). FIG. 4 shows that 18,19-dinor-2MP has little, if any, activity in mobilizing calcium from bone, and its activity is about equivalent to 2MP. Administration of 18,19-dinor-2MP at 780 pmol/day for 4 consecutive days did not result in mobilization of bone calcium, and increasing the amount of 18,19-dinor-2MP to 2340 pmol/day or to 7020 pmol/day was also without any substantial effect.

Intestinal calcium transport was evaluated in the same groups of animals using the everted gut sac method (FIG. 5). These results show that the compound 18,19-dinor-2MP does not promote intestinal calcium transport when administered at 780 pmol/day, 2340 pmol/day or 7020 pmol/day, whereas 1,25(OH)$_2$D$_3$ promotes a significant increase at the 780 pmol/day dose, and 2MP also provides a significant increase at a 2340 pmol/day dose. Thus, it may be concluded that 18,19-dinor-2MP is essentially devoid of intestinal calcium transport activity at the tested doses.

These results illustrate that 18,19-dinor-2MP is an excellent candidate for numerous human therapies as described herein, and that it may be particularly useful in a number of circumstances such as suppression of secondary hyperparathyroidism of renal osteodystrophy, autoimmune diseases, cancer, and psoriasis. 18,19-dinor-2MP is an excellent candidate for treating psoriasis because: (1) it has significant VDR binding, transcription activity and cellular differentiation activity; (2) it is devoid of hypercalcemic liability unlike 1,25(OH)$_2$D$_3$; and (3) it is easily synthesized. Since 18,19-dinor-2MP has significant binding activity to the vitamin D receptor, but has little ability to raise blood serum calcium, it may also be particularly useful for the treatment of secondary hyperparathyroidism of renal osteodystrophy.

These data also indicate that the compound 18,19-dinor-2MP of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound 18,19-dinor-2MP of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I may be formulated for pharmaceutical applications as a solution in innocuous solvents, or as an emulsion, suspension or dispersion in suitable solvents or carriers, or as pills, tablets or capsules, suppositories, or aerosols together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly 18,19-dinor-2MP, may be administered orally, topically, parenterally, rectally, nasally, sublingually or transdermally. The compounds may be advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.0 μg to 1000 μg per day of the compounds I, particularly 18,19- dinor-2MP, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatments comprise an effective amount of the compounds I, particularly 18,19-dinor-2MP, as defined by the above formula I and Ia as the active ingredient, and a suitable carrier. An effective amount of such compounds for use in accordance with this invention is from about 0.01 µg to about 1000 µg per gm of composition, preferably from about 0.1 µg to about 500 µg per gram of composition, and may be administered topically, transdermally, orally or parenterally in dosages of from about 0.01 µg/day to about 1000 µg/day, and preferably from about 0.1 µg/day to about 500 µg/day.

The compounds I, particularly 18,19-dinor-2MP, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly 18,19-dinor-2MP, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

What is claimed is:

1. A compound having the formula:

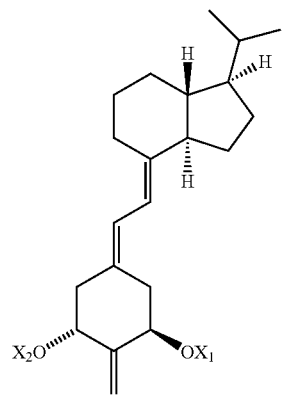

where $X_1$ and $X_2$, which may be the same or different, are each selected from hydrogen or a hydroxy-protecting group.

2. The compound of claim 1 wherein $X_2$ is hydrogen.

3. The compound of claim 1 wherein $X_1$ is hydrogen.

4. The compound of claim 1 wherein $X_1$ and $X_2$ are both t-butyldimethylsilyl.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 µg to about 1000 µg per gram of composition.

7. The pharmaceutical composition of claim 5 wherein said effective amount comprises from about 0.1 µg to about 500 µg per gram of composition.

8. 2-methylene-18,19-dinor-1α-hydroxy-homopregnacalciferol having the formula:

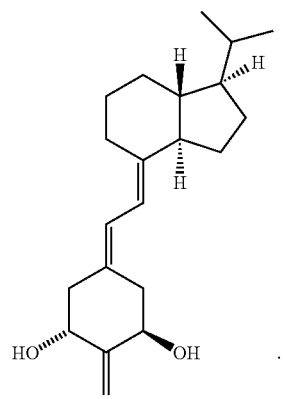

9. A pharmaceutical composition containing an effective amount of 2-methylene-18,19-dinor-1α-hydroxy-homopregnacalciferol together with a pharmaceutically acceptable excipient.

10. The pharmaceutical composition of claim 9 wherein said effective amount comprises from about 0.01 μg to about 1000 μg per gram of composition.

11. The pharmaceutical composition of claim 9 wherein said effective amount comprises from about 0.1 μg to about 500 μg per gram of composition.

12. A method of treating psoriasis comprising administering to a subject with psoriasis an effective amount of a compound having the formula:

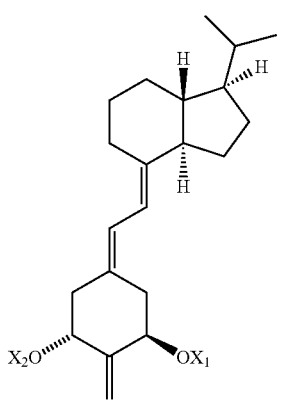

where $X_1$ and $X_2$, which may be the same or different, are each selected from hydrogen or a hydroxy-protecting group.

13. The method of claim 12 wherein the compound is administered orally.

14. The method of claim 12 wherein the compound is administered parenterally.

15. The method of claim 12 wherein the compound is administered transdermally.

16. The method of claim 12 wherein the compound is administered topically.

17. The method of claim 12 wherein the compound is administered rectally.

18. The method of claim 12 wherein the compound is administered nasally.

19. The method of claim 12 wherein the compound is administered sublingually.

20. The method of claim 12 wherein the compound is administered in a dosage of from about 0.01 μg/day to about 1000 μg/day.

21. The method of claim 12 wherein the compound is 2-methylene-18,19-dinor-1α-hydroxy-homopregnacalciferol having the formula:

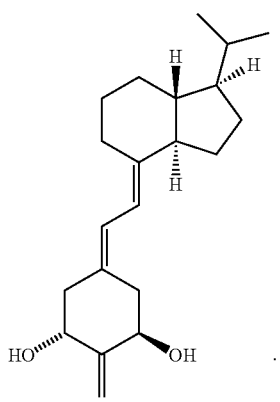

22. A method of treating a disease selected from the group consisting of leukemia, colon cancer, breast cancer, skin cancer or prostate cancer comprising administering to a subject with said disease an effective amount of a compound having the formula:

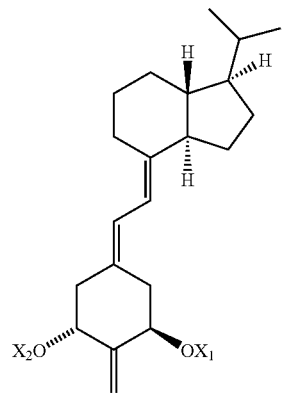

where $X_1$ and $X_2$, which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 μg/day to about 1000 μg/day.

30. The method of claim 22 wherein the compound is 2-methylene-18,19-dinor-1α-hydroxy-homopregnacalciferol having the formula:

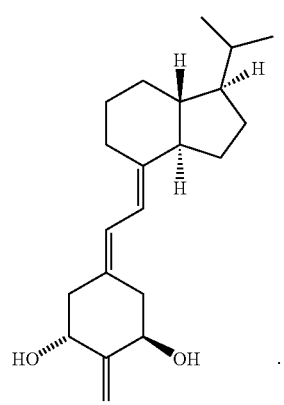

31. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

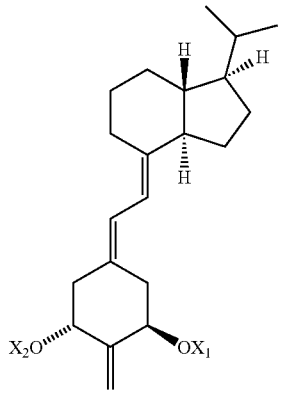

where $X_1$ and $X_2$, which may be the same or different, are each selected from hydrogen or a hydroxy-protecting group.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 wherein the compound is 2-methylene-18,19-dinor-1α-hydroxy-homopregnacalciferol having the formula:

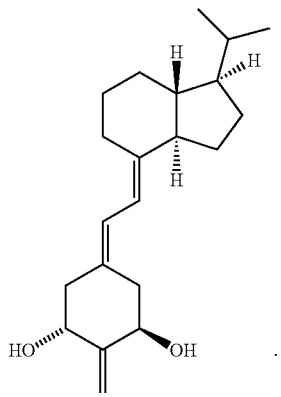

40. A method of treating an inflammatory disease selected from the group consisting of rheumatoid arthritis, asthma, and inflammatory bowel diseases, comprising administering to a subject with said disease an effective amount of a compound having the formula:

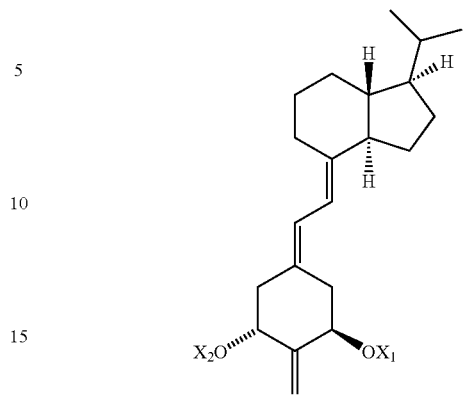

where $X_1$ and $X_2$, which may be the same or different, are each selected from hydrogen or a hydroxy-protecting group.

41. The method of claim 40 wherein the compound is administered orally.

42. The method of claim 40 wherein the compound is administered parenterally.

43. The method of claim 40 wherein the compound is administered transdermally.

44. The method of claim 40 wherein the compound is administered rectally.

45. The method of claim 40 wherein the compound is administered nasally.

46. The method of claim 40 wherein the compound is administered sublingually.

47. The method of claim 40 wherein the compound is administered in a dosage of from about 0.01 μg/day to about 1000 μg/day.

48. The method of claim 40 wherein the compound is 2-methylene-18,19-dinor-1α-hydroxy-homopregnacalciferol having the formula:

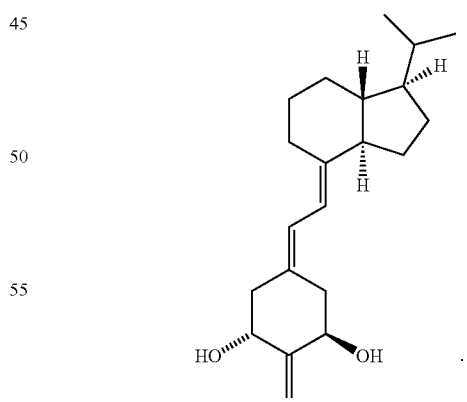

49. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

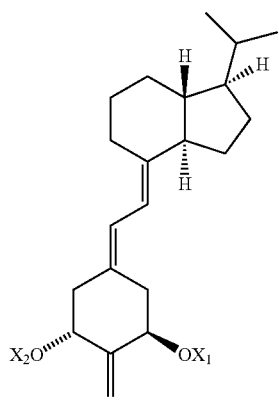

where $X_1$ and $X_2$, which may be the same or different, are each selected from hydrogen or a hydroxy-protecting group.

50. The method of claim 49 wherein the compound is administered orally.

51. The method of claim 49 wherein the compound is administered parenterally.

52. The method of claim 49 wherein the compound is administered transdermally.

53. The method of claim 49 wherein the compound is administered topically.

54. The method of claim 49 wherein the compound is administered rectally.

55. The method of claim 49 wherein the compound is administered nasally.

56. The method of claim 49 wherein the compound is administered sublingually.

57. The method of claim 49 wherein the compound is administered in a dosage of from about 0.01 µg/day to about 1000 µg/day.

58. The method of claim 49 wherein the compound is 2-methylene-18,19-dinor-1α-hydroxy-homopregnacalciferol having the formula:

59. A method of treating renal osteodystrophy comprising administering to a subject with renal osteodystrophy an effective amount of a compound having the formula:

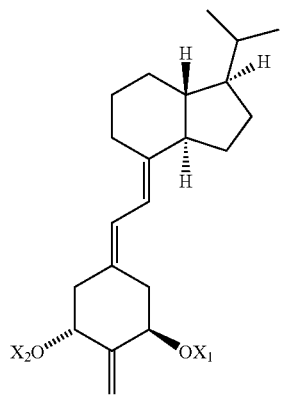

where $X_1$ and $X_2$, which may be the same or different, are each selected from hydrogen or a hydroxy-protecting group.

60. The method of claim 59 wherein the compound is administered orally.

61. The method of claim 59 wherein the compound is administered parenterally.

62. The method of claim 59 wherein the compound is administered transdermally.

63. The method of claim 59 wherein the compound is administered rectally.

64. The method of claim 59 wherein the compound is administered nasally.

65. The method of claim 59 wherein the compound is administered sublingually.

66. The method of claim 59 wherein the compound is administered in a dosage of from about 0.01 µg/day to about 1000 µg/day.

67. The method of claim 59 wherein the compound is 2-methylene-18,19-dinor-1α-hydroxy-homopregnacalciferol having the formula:

68. A method of treating or preventing obesity of an animal, inhibiting adipocyte differentiation, inhibiting SCD-1 gene transcription, and/or reducing body fat in an animal comprising administering to an animal in need thereof an effective amount of a compound having the formula:

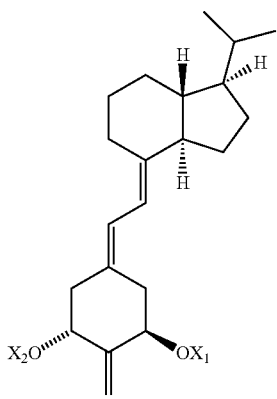

where $X_1$ and $X_2$, which may be the same or different, are each selected from hydrogen or a hydroxy-protecting group.

69. The method of claim 68 wherein the compound is administered orally.

70. The method of claim 68 wherein the compound is administered parenterally.

71. The method of claim 68 wherein the compound is administered transdermally.

72. The method of claim 68 wherein the compound is administered rectally.

73. The method of claim 68 wherein the compound is administered nasally.

74. The method of claim 68 wherein the compound is administered sublingually.

75. The method of claim 68 wherein the compound is administered in a dosage of from about 0.01 μg/day to about 1000 μg/day.

76. The method of claim 68 wherein the compound is 2-methylene-18,19-dinor-1α-hydroxy-homopregnacalciferol having the formula:

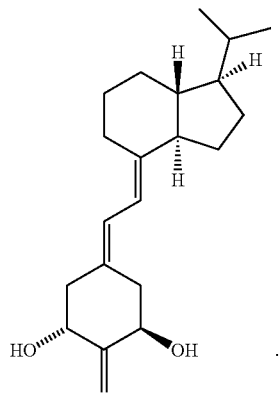

77. The method of claim 68 wherein the animal is a human.

78. The method of claim 68 wherein the animal is a domestic animal.

79. The method of claim 68 wherein the animal is an agricultural animal.

* * * * *